United States Patent [19]

McDonald

[11] Patent Number: 5,135,954
[45] Date of Patent: Aug. 4, 1992

[54] USE OF FORMOTEROL FOR TREATMENT OF TISSUE INJURY

[75] Inventor: Donald M. McDonald, San Francisco, Calif.

[73] Assignee: The Regents of the University of California, Oakland, Calif.

[21] Appl. No.: 705,103

[22] Filed: May 24, 1991

[51] Int. Cl.$^5$ .............................. A01N 37/18
[52] U.S. Cl. .................................... 514/630
[58] Field of Search ........................ 514/630

[56] References Cited

U.S. PATENT DOCUMENTS

| | | | |
|---|---|---|---|
| 3,994,974 | 11/1976 | Murakami et al. | 260/562 |
| 4,380,534 | 4/1983 | Fukui et al. | 424/38 |
| 4,685,911 | 8/1987 | Konno et al. | 604/897 |
| 4,841,161 | 3/1989 | Jinks et al. | 424/45 |
| 4,879,119 | 11/1989 | Konno et al. | 424/449 |
| 4,911,707 | 3/1990 | Heiber et al. | 424/449 |
| 4,917,676 | 4/1990 | Heiber et al. | 424/449 |
| 4,975,466 | 12/1990 | Bottcher et al. | 514/630 |

OTHER PUBLICATIONS

Murase, et al. Chem. Pharm. Bull. 25 1368 (1977).
Arfors, et al., Acta Physiol. Scand., Suppl. 463, 93 (1979).
Beets, et al., Br. J. Pharmac. 70, 461 (1980).
Erjefalt, et al., Agents and Actions 16, 9 (1985).
Svensjo, et al., Agents and Actions 16, 19 (1985).
Martling, et al., Anesthesiology 68, 350 (1988).
Boschetto, et al., Am. Rev. Respir. Dis. 139, 416 (1989).
Tokuyama et al., European Journal of Pharmacology 193, 35 (1991).
Tomioka et al., Arch. Int. Pharmacodyn 250, 279 (1981).
Tomioka et al., Arch. Int. Pharmacodyn. 267, 91 (1984).

Primary Examiner—Alan Siegel
Assistant Examiner—Rebecca Coole
Attorney, Agent, or Firm—Walter H. Dreger

[57] ABSTRACT

Formoterol, a known $\beta$-adrenergic agonist, which, when administered intravascularly, has been found to profoundly reduce plasma extravasation resulting from tissue damage consequent to injury induced, for example, by surgery.

3 Claims, 1 Drawing Sheet

USE OF FORMOTEROL FOR TREATMENT OF TISSUE INJURY

FIELD OF THE INVENTION

The present invention is directed to a new method of use of formoterol, the generic name of a specific $\beta$-adrenergic agonist. One chemical name of formoterol is ($\pm$)-N-[2-hydroxy-5-[1-hydroxy-2-[[2-(4-methoxyphenyl)-1-methylethyl]amino]-ethyl]phenyl]formamide of the formula:

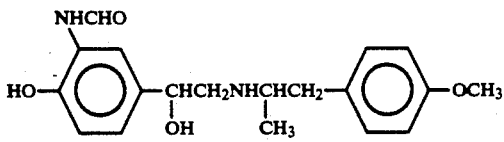

Formoterol was believed first described in U.S. Pat. No. 3,994,974, and various foreign counterparts thereof, as a $\beta$-adrenoreceptor stimulating catecholamine analog with selective bronchodilator activity. Its preparation and its physical and biological parameters have been published. It is therapeutically categorized as an anti-asthmatic. See also Murase, et. al., *Chem. Pharm. Bull.* 25, 1368 (1977) that reports on a number of $\beta$-adrenoreceptor stimulants including formoterol (BD-40-A).

BACKGROUND OF THE INVENTION

After the initial discovery of formoterol, it has enjoyed the attention of a good deal of research, attested by numerous publications that need not be detailed here as they are readily available to the art-skilled.

Formoterol has been used as a bronchodilator by its direct administration to the lungs of affected patients. In addition, a number of different means of administration have been detailed in the art, and for examples, there are cited U.S. Pat. Nos. 4,685,911, 4,879,119, 4,911,707 and U.S. Pat. No. 4,917,676 that address transdermal means of administration topically; U.S. Pat. No. 4,380,534 addressing a solid composition incorporating formoterol; U.S. Pat. No. 4,814,161 detailing a particular aerosol form; and U.S. Pat. No. 4,975,466 that discloses the topical administration of formoterol. The medical literature on formoterol is also extensive, detailing its use as a $\beta$-adrenergic agonist bronchodilator.

A number of these literature references will be considered more particularly in respect of the present invention as they serve as a point of departure signalled by the new use of formoterol which is the predicate of the present invention.

Several studies reported in the literature provide findings consistent with formoterol manifesting an anti-edema effect. For example, formoterol inhibits the extravasation of Evans blue associated with passive cutaneous anaphylaxis in rats. Formoterol also has been reported to inhibit the increase in lung weight caused by the inhalation of histamine aerosol in guinea pigs. A recent study reports that pre-treatment of guinea pigs with aerosolized formoterol significantly reduces the amount of Evans blue extravasation into the trachea following exposure to histamine aerosol. Further, formoterol injected into the skin of normal humans reduces the size of wheals produced by intradermal injections of histamine. There are no known reports of the intravascular injection of formoterol for any related purpose.

A number of articles report on the inhibition of chemically-induced extravastion by terbutaline, a $\beta$-adrenergic bronchodilator. For example, Arfors, et. al., *Acta Physiol. Scand., Suppl* 463 93 (1979) reports on the intravenous administration of terbutaline in reversing topically induced inflammation. Beets, et. al. *Br. J. Pharmac.* 70, 46(1980) similarly reports on the inhibition of drug-induced extravasation by intravenously administered terbutaline. Erjefalt, et. al., *Agents and Actions* 16, 9 (1985) report on the inhibition of capsaicin-induced inflammatory response in lower airways by measuring the microvascular effects of terbutaline given intravenously as a pre-treatment. See also the collective works of Svensjo, et. al., e.g., *Agents and Actions* 16, 19 (1985).

Contrary to the foregoing information with respect to terbutaline, Martling, et. al., *Anesthesiology* 68, 350 (1988) found that the selective intravenous administration of the $\beta$-adrenergic agonist terbutaline did not significantly change the Evans blue extravasation in rat trachea. Further, the related compound albuterol failed to inhibit dye leakage at any dose studied, as reported by Boschetto, et. al., *Am. Rev. Resoir. Dis.* 139, 416 (1989) who obtained similar negative results after intravenous administration of albuterol. Boschetto, et. al., in explaining that their results were different from those earlier reported with terbutaline, state, without experimental support, that different routes of administration may be implicated.

Interestingly, Tokuyama, et. al., *European Journal of Pharmacology* 193, 35 (1991), found that inhaled formoterol aerosol inhibits histamine induced air flow obstruction and airway microvascular leakage and acknowledged that their results were in conflict with those of Boschetto, et. al., suggesting again that the different routes of administration may be implicated.

Tomioka, et. al. *Arch. Int. Pharmacodyn* 250, 279 (1981) bluntly stated that their results in rats of intravenously injected formoterol inhibiting passive cutaneous anaphylaxis, one manifestation of which is leaky blood vessels, are not due to a direct effect of the drug on vascular permeability. Indeed, in a later article by the same authors there is no mention of the anti-edema action of formoterol by any means. See Tomioka, et. al. *Arch. Int. Pharmoacodyn*, 267, 91 (1984).

The group of publications summarized above documents the disparity of the results of various experiments which have examined the possible anti-edema action of $\beta$-adrenergic agonists, thus leaving an impression of unpredictability as to the relevance of such parameters as the effectiveness of each particular drug, the route of administration, the cause of the increased vascular permeability being treated, and the mechanism of any observed effects of the drug.

SUMMARY OF THE INVENTION

The present invention is based upon the fundamental finding that formoterol, when administered intravascularly, is useful for preventing or decreasing plasma extravasation occurring when tissues are damaged by trauma or other injury. This effect is considered surprising in view of the art which would not have reasonably predicted such results.

Thus, in one aspect, the present invention is directed to a method of preventing or decreasing plasma extravasation associated with tissue damage due to trauma or other injury comprising administering an effective amount of formoterol intravascularly to an individual suffering such tissue damage.

The present invention is directed to that fundamental predicate in all of its associated aspects and embodiments including pharmaceutical compositions suitable for such intravascular treatment, and medical protocol useful in effecting this method of therapeutic treatment. The fundamental experiments upon which this invention is based demonstrate that formoterol has a very generalized anti-edema effect through which it inhibits the plasma extravasation produced by other inflammatory stimuli as well. In particular, it was found that formoterol prevents or decreases plasma extravasation associated with tissue injury produced by surgical incisions and mechanical trauma, and the like, and that this effect is produced by administering formoterol intravascularly.

The anti-edema effect of formoterol described herein has the clinical usefulness of preventing or decreasing plasma extravasation, particularly in cases of rather severe tissue damage. For purposes of the present invention, effective amounts of formoterol are administered to patients suffering from injury-induced tissue damage, characteristic of that inflicted by such external agents as trauma, burns, frostbite, noxious chemicals, irradiation, and so forth. For an example, the present invention is particularly useful clinically for treatment before and/or after surgical procedures.

The term "preventing or decreasing," or grammatical equivalents, includes prophylactic and therapeutic utility, and therefore, is synonymous also with inhibiting, reversing (and the like) plasma extravasation associated with tissue damage.

Formoterol is administered intravascularly in "an effective amount" which is that amount that results in the end-point of reduced or inhibited plasma extravasation associated with the characterized tissue injury. The term "an effective amount" thus has a functional definition. The intravascular route of administration contemplates the full range of methods including injection of a bolus or continuous infusion. The effective amount administered ranges from about 0.01 $\mu$g to about 100 $\mu$g per kilogram of body weight of the individual being treated. As formoterol is a commercially available drug, toxicity and other clinical data are available to the art-skilled. Thus, as the endpoint of the present treatment is clinically observable, the functional language as to the amount that is useful herein is justified.

It is contemplated that derivatives of formoterol may function equivalently, and as such, are intended to be within the general scope of this invention otherwise focusing on formoterol per se. Similarly contemplated is the administration of formoterol in various finished pharmaceutical forms that are non-toxic and otherwise physiologically acceptable. These forms will be suitable for intravascular administration and the skill of the art is available for methods by which they can be formulated. For example, lipophilic emulsions of formoterol may be preferred formulations that are physiologically acceptable.

The particular animal model used herein is considered predictive of analogous clinical effectiveness in a human being. Formoterol is administered clinically, albeit in aerosol (topical) or oral form, and therefore, its clinical utility in that respect in man has been proved. Evidence is in hand for a rat model which demonstrates that the anti-edema effect of intravascularly administered formoterol is at the level of the endothelial cell. Intravascular administration assures systemic effects for preventing or decreasing plasma extravasation at all sites of tissue injury, not just at a single locus and not limited to tissues accessible by topical or aerosol administration. An analogous effect could reasonably be expected in humans based on the similarities of the other actions of formoterol in rats and humans.

The present invention is necessarily defined within certain functional parameters. Having described the invention as the predicate of unexpected inhibition or reversal of plasma extravasation by intravascular administration of formoterol, and having described particular means by which one can effect that, it is well within the skill of the art to modify the specific parameters without departing from the spirit of the invention. Therefore, the present invention is intended to cover all legally cognizable equivalents of the particularly preferred embodiments that are described as follows:

DETAILED DESCRIPTION

DESCRIPTION OF A PREFERRED EMBODIMENT

Figure 1:
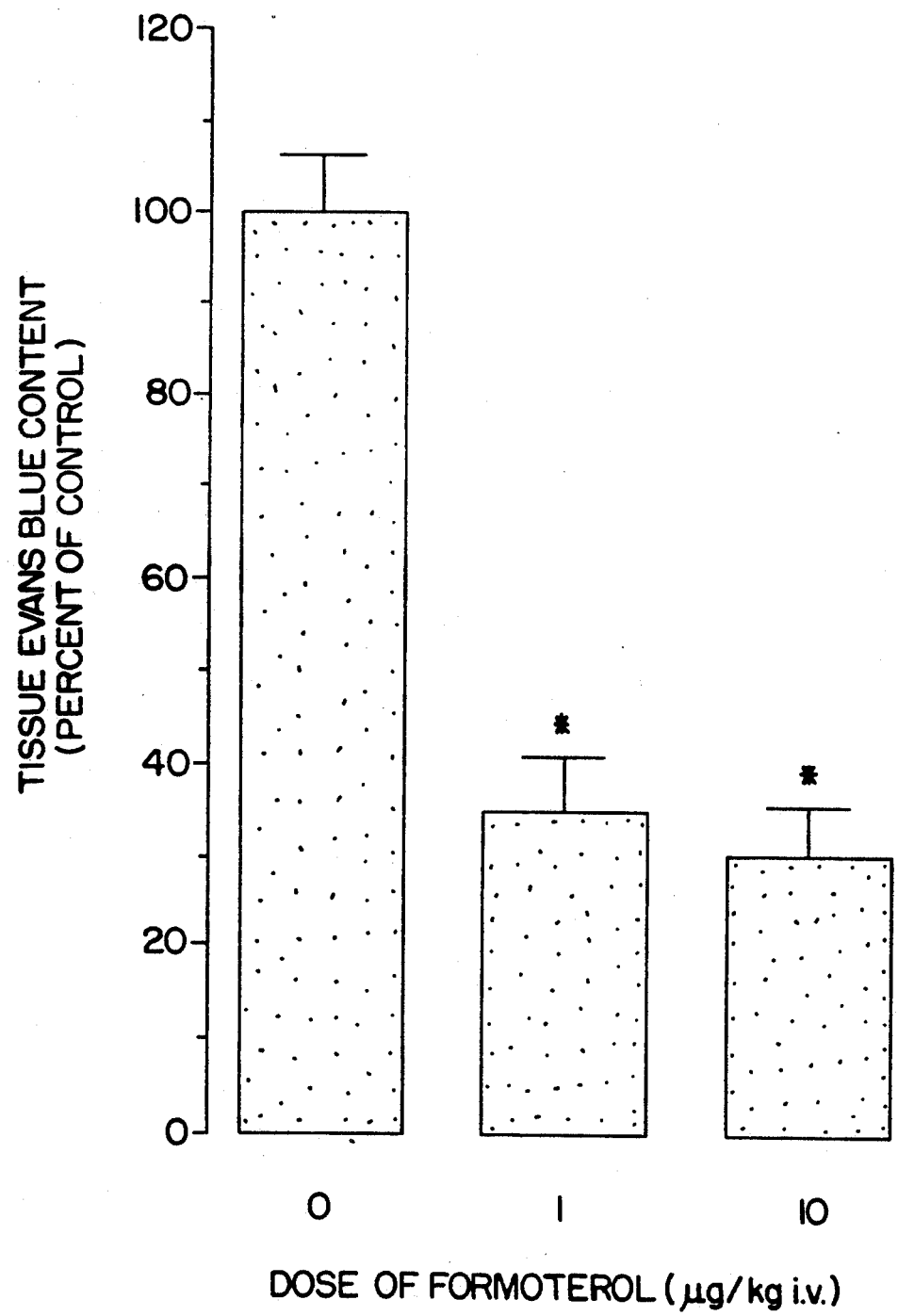
FIG. 1 is a histogram showing the anti-edema action of formoterol at surgical wounds in the skin of rats (N =4 per group). The skin incisions were made in the groin at time =0 min. The formoterol or its vehicle was injected intravenously at 2 min. Evans blue dye was injected as a tracer at 7 min., and specimens of subcutaneous connective tissue were removed from the region of the incisions after the rats were perfused with fixative at 13 min. Asterisks mark values that were significantly different from the control value, as determined by one-way analysis of variance (P <0.05).

The present invention is based upon the discovery that formoterol inhibits the plasma extravasation associated with tissue injury produced by surgical incisions and mechanical trauma, and so forth. The unexpected finding that forms the basis of the present invention was that there was conspicuously less extravasated Monastral blue and Evans blue in the region of surgical wounds in the animals treated with formoterol (1 or 10 $\mu$g/kg i.v.) than there was in the animals treated with the saline vehicle control. None of these effects of formoterol has been described heretofore. The observations indicate that formoterol has the clinical utility of reducing plasma extravasation in tissues injured by trauma such as from surgical incisions, burns, or exposure to irritants, noxious agents or allergens.

In the original experiment underlying the present invention it was discovered that formoterol inhibits plasma extravasation associated with tissue injury produced by surgical incisions and mechanical trauma.

These surgical wounds included skin incisions and dissections of subcutaneous tissues and muscles that were and to expose blood vessels for intravenous injections.

The unexpected finding was that there was conspicuously less extravasated Monastral blue and Evans blue in the region of these surgical wounds in the rats treated with formoterol (1 or 10 $\mu$g/kg i.v.) compared with rats treated with the saline vehicle.

Measurements of the Evans blue content of the subcutaneous connective tissue obtained from surgical wounds in the groin revealed that the amount of extravasation was reduced 65±6% (mean ±SE) in rats treated with formoterol in a dose of 1 μg/kg i.v. and reduced 69 ±5% in rats receiving a dose of 10 μg/kg i.v. (see FIG. 1).

Also observed was a reduction in the amount of extravasated tracer in skeletal muscles near the vagus nerve and other structures exposed by the wounds.

This decrease in plasma extravasation in the region of the wounds was evident when the formoterol was injected several minutes after the wounds were made. Therefore, formoterol can evidently reverse the increase in vascular permeability produced by tissue trauma.

EXAMPLES

A. Protocol

Pathogen-free male rats of the F-344 strain were anesthetized with sodium methohexital (60 mg/kg i.p.), and then the femoral veins and the cervical vagus nerve or the trachea were exposed through skin incisions.

2. Thereafter, the rats received an injection of formoterol (1, 10, or 100 μg/kg i.v.) or 0.9% NaCl (1 ml/kg), the vehicle used to dissolve the formoterol.

3. Five minutes later the rats received an intravenous injection of a mixture Evans blue dye and Monastral blue pigment (30 each in 0.9% NaCl) to assess vascular permeability.

4. Six minutes after the injection of the tracers, the rats were perfused through the heart with 1% paraformaldehyde fixative to wash out the intravascular tracers and to preserve the tissues. The region of the wounds was inspected and then tissue specimens were removed and weighed. Evans blue was extracted from the tissue specimens with Suramin in methanol and measured by spectrophotometry, using a standard curve for calibration. Some tissue specimens were prepared as whole mounts to determine the distribution of extravasated Monastral blue in the wall of the abnormally permeable blood vessels.

B. Results

1. In anesthetized rats in which the blue tracers were injected intravenously to detect sites of increased vascular permeability, blue regions of extravasation of the tracers were evident in the regions of all surgical incisions. This finding was not surprising because the tissue irritation and damage due to the surgery would be expected to cause a localized increase in vascular permeability.

2. In these rats, the injured blood vessels labeled by the blue tracers were postcapillary venules in the skin, subcutaneous connective tissue, muscle, trachea, and other structures exposed by the wounds.

3. The unexpected finding was that there was conspicuously less extravasated blue tracer in the region of the surgical wounds in the rats treated with formoterol (1, 10 or 100 μg/kg i.v.).

4. For example, measurements of the Evans blue content of the subcutaneous connective tissue obtained from surgical wounds in the groin revealed that the amount of extravasation was reduced by 65% after an intravenous dose of 1 μg/kg of formoterol.

5. Similarly, there was a reduction in the amount of extravasated tracer in muscle, trachea, and other structures exposed by the wounds.

6. This decrease in plasma extravasation in the region of the wounds was evident even when the formoterol was injected several minutes after the wounds were made.

Tables 1 and 2 detail the results:

TABLE 1

Evans Blue (EB) Content of Groin Connective Tissue at Surgical Wound: Effect of Formoterol
FORMOTEROL EXPERIMENTS
Slope of EB curve - 77.83762376

| Rat Number | Formoterol (μ/kg i.v.) | Tissue from wound region | Body wt (g) | Tissue wt (μg) | Optical Density | Evans Blue (μg/ml) | Evans Blue (ng/tissue) | Evans Blue (ng/μg tissue) | % of Evans blue control mean |
|---|---|---|---|---|---|---|---|---|---|
| R03 042590 | 0 ug/kg | groin subq tissue | 250 | 180.0 | 0.0775 | 0.001073 | 3219.7 | 17.8870 | 100.65 |
| R05 042590 | 0 ug/kg | groin subq tisue | 247 | 210.0 | 0.1057 | 0.001463 | 4389.8 | 20.9039 | 117.62 |
| R07 042590 | 0 ug/kg | groin subq tissue | 244 | 130.0 | 0.0490 | 0.000679 | 2035.7 | 15.6589 | 88.11 |
| R09 042590 | 0 ug/kg | groin subq tissue | 250 | 201.0 | 0.0805 | 0.001115 | 3344.3 | 16.6383 | 93.62 |
| | | mean | 248 | 180.25 | 0.078 | 0.001082 | 3247 | 17.772 | 100.000 |
| | | S.D. | 2.87 | 35.78 | 0.023 | 0.000321 | 963 | 2.278 | 12.820 |
| | | S.E. | 1.44 | 17.89 | 0.0116 | 0.0002 | 482 | 1.139 | 6.410 |
| | | N | 4 | 4 | 4 | 4 | 4 | 4 | 4 |
| R02 050290 | 1 ug/kg | groin subq tissue | 242 | 241.5 | 0.0203 | 0.000261 | 783.6827 | 3.2451 | 18.26 |
| R04 050290 | 1 ug/kg | groin subq tissue | 242 | 147.2 | 0.0307 | 0.000394 | 1181.9477 | 8.0295 | 45.18 |
| R06 050290 | 1 ug/kg | groin subq tissue | 246 | 146.2 | 0.0270 | 0.000347 | 1040.6279 | 7.1178 | 40.05 |
| R08 050290 | 1 ug/kg | groin subq tissue | 236 | 133.5 | 0.0230 | 0.000295 | 886.4608 | 6.6402 | 37.36 |
| | | mean | 242 | 167.10 | 0.025 | 0.000324 | 973 | 6.258 | 35.214 |
| | | S.D. | 4.12 | 49.99 | 0.005 | 0.000058 | 175 | 2.090 | 11.759 |
| | | S.E. | 2.06 | 25.00 | 0.0023 | 0.0000 | 87 | 1.045 | 5.879 |
| | | N | 4 | 4 | 4 | 4 | 4 | 4 | 4 |
| R03 050290 | 10 ug/kg | groin subq tissue | 239 | 298.8 | 0.0490 | 0.000630 | 1888.5469 | 6.3204 | 35.56 |
| R05 050290 | 10 ug/kg | groin subq tissue | 240 | 236.4 | 0.0437 | 0.000561 | 1682.9907 | 7.1193 | 40.06 |
| R07 050290 | 10 ug/kg | groin subq tissue | 246 | 216.0 | 0.0293 | 0.000377 | 1130.5587 | 5.2341 | 29.45 |
| R09 050290 | 10 ug/kg | groin subq tissue | 240 | 222.5 | 0.0177 | 0.000227 | 680.9047 | 3.0602 | 17.22 |
| | | mean | 241 | 243.43 | 0.035 | 0.000449 | 1346 | 5.434 | 30.573 |
| | | S.D. | 3.20 | 37.88 | 0.014 | 0.000182 | 547 | 1.761 | 9.907 |
| | | S.E. | 1.60 | 18.94 | 0.0071 | 0.0001 | 273 | 0.880 | 4.954 |
| | | N | 4 | 4 | 4 | 4 | 4 | 4 | 4 |
| R02 042590 | 100 ug/kg | groin subq tissue | 247 | 161.7 | 0.0310 | 0.000429 | 1287.9 | 7.9645 | 44.82 |
| R04 042590 | 100 ug/kg | groin subq tissue | 254 | 206.6 | 0.0215 | 0.000298 | 893.2 | 4.3233 | 24.33 |
| R06 042590 | 100 ug/kg | groin subq tissue | 241 | 256.3 | 0.0437 | 0.000605 | 1814.1 | 7.0780 | 39.83 |
| R08 042590 | 100 ug/kg | groin subq tissue | 244 | 260.9 | 0.0455 | 0.000630 | 1890.3 | 7.2451 | 40.77 |
| | | mean | 247 | 221.38 | 0.035 | 0.000490 | 1471 | 6.653 | 37.434 |
| | | S.D. | 5.57 | 46.77 | 0.011 | 0.000156 | 469 | 1.600 | 9.002 |
| | | S.E. | 2.78 | 23.38 | 0.0056 | 0.0001 | 235 | 0.800 | 4.501 |

TABLE 1-continued

Evans Blue (EB) Content of Groin Connective Tissue at Surgical Wound: Effect of Formoterol
FORMOTEROL EXPERIMENTS
Slope of EB curve - 77.83762376

| Rat Number | Formoterol (μ/kg i.v.) | Tissue from wound region | Body wt (g) | Tissue wt (μg) | Optical Density | Evans Blue (μg/ml) | Evans Blue (ng/tissue) | Evans Blue (ng/μg tissue) | % of Evans blue control mean |
|---|---|---|---|---|---|---|---|---|---|
| | | N | 4 | 4 | 4 | 4 | 4 | 4 | 4 |

TABLE 2

Effect of Formoterol on Evans Blue (EB) extravasation from a surgical wound

One Factor Analysis of Variance (ANOVA) $X_1$: Formoterol $Y_2$: EB ng/μg tis
Analysis of Variance Table

| Source | Degrees of Freedom (DF) | Sum Squares | Mean Square | F-test |
|---|---|---|---|---|
| Between groups | 3 | 410.77 | 136.923 | 35.99 |
| Within groups | 12 | 45.653 | 3.804 | p = .0001 |
| Total | 15 | 456.423 | | |

Model II estimate of between component variance - 44.373

One Factor ANOVA $X_1$: Formoterol $Y_2$: EB ng/μg tis

| Group | Count | Mean | Std. Dev. | Std. Error |
|---|---|---|---|---|
| 0 ug/kg | 4 | 17.772 | 2.278 | 1.139 |
| 1 μg/kg | 4 | 6.258 | 2.09 | 1.045 |
| 10 μg/kg | 4 | 5.434 | 1.761 | .88 |
| 100 ug/kg | 4 | 6.653 | 1.6 | .8 |

One Factor ANOVA $X_1$: Formoterol $Y_2$: EB ng/μg tis

| Comparison | Mean Diff. | Fisher PLSD | Scheffe F-test | Dunnett t |
|---|---|---|---|---|
| 0 ug/kg vs. 1 μg/kg | 11.514 | 3.005* | 23.231* | 8.348 |
| 0 ug/kg vs. 10 ug/kg | 12.339 | 3.005* | 26,678* | 8.946 |
| 0 ug/kg vs 100 ug/kg | 11.119 | 3.005* | 21.666* | 8.062 |
| 1 μg/kg vs. 10 μg/kg | .825 | 3.005 | .119 | .598 |
| 1 μg/kg vs. 100 ug/kg | −.395 | 3.005 | .027 | .286 |

*Significant at 95%

Concluding Remarks

The foregoing description details specific methods that can be employed to practice the present invention. Having detailed such specific methods initially used to produce the unexpected result of inhibiting the plasma extravasation by intravascular administration of formoterol, as described herein, and having detailed further disclosure as to specific systems, and equivalent components and means to effect that, those skilled in the art will well enough know how to devise alternative reliable means for arriving at the same results and for extending this information to other legally cognizable equivalents. Thus, however detailed the foregoing may appear in text, it should not be construed as limiting the overall scope hereof; rather, the ambit of the present invention is to be governed only by the lawful construction of the appended claims.

I claim:

1. A method for preventing or decreasing extravasation associated with tissue damage due to injury comprising administering an effective amount of formoterol intravascularly to an individual suffering such tissue damage.

2. A method according to claim 1 wherein said formoterol is in a physiologically acceptable pharmaceutical form.

3. The method according to claim 2 wherein said effective amount ranges from about 0.01 to about 100 μg/kg of individual body weight.

* * * * *